United States Patent [19]

Tsuruta et al.

[11] Patent Number: 5,066,582

[45] Date of Patent: Nov. 19, 1991

[54] METHOD AND APPARATUS FOR THE MEASUREMENT OF ANALYTE SUBSTANCES

[75] Inventors: Hitoshi Tsuruta; Hideaki Yamada, both of Kurashiki; Michihiro Nakamura, Soja, all of Japan

[73] Assignee: Kuraray Co., Ltd., Kurashiki, Japan

[21] Appl. No.: 311,779

[22] Filed: Feb. 17, 1989

[30] Foreign Application Priority Data

Feb. 19, 1988 [JP] Japan .................................. 63-38274

[51] Int. Cl.[5] .......................................... G01N 33/543
[52] U.S. Cl. .................................... 435/7.1; 436/163; 204/403; 204/433; 422/56
[58] Field of Search ...................... 436/163; 422/82.03, 422/82.04, 56-58; 204/403, 433; 435/7.1

[56] References Cited

U.S. PATENT DOCUMENTS

| 4,318,709 | 3/1982 | Falb | 23/230 |
| 4,713,165 | 12/1987 | Conover | 204/403 |

FOREIGN PATENT DOCUMENTS 0170375 6/1985 European Pat. Off. .
0328380 10/1988 European Pat. Off. .

OTHER PUBLICATIONS

Chemical Abstracts, vol. 96, 1982 p. 96, abstract No. 155710n, Columbus, Ohio, U.S.; M. Mascini et al.: "pH Electrode-Based Enzyme Immunoassay for the Determination of Human Chorionic Gonadotropin" & Anal. Lett. 1982 15(B2), 101-113.

Chemical Abstracts, vol. 100, 1984, p. 270 abstract No. 153448k, Columbus, Ohio, U.S.; & JP-A-59 28 648 Kuraray Co. Ltd.) 15-02-84.

Chemical Abstracts, vol. 90, 1979, p. 244, abstract No. 164334w, Columbus, Ohio, U.S.; & JP-A-78 149 392 (Kuraray Co., Ltd.) 26-12-1978.

Chemical Abstracts, vol. 103, 1985, p. 394, abstract No. 209457u, Columbus, Ohio, U.S.; R. R. Premier et al.: "An Evaluation of the Use of a pH Indicator for the Detection of Beta-Lactamase in Enzyme Immunoassay", & J. Immunol. Methods 1985, 83(2) 371-377.

Boitieux, J-L, and Thomas, D; *Clinical Biochemistry*, 17, 151-156.

*Primary Examiner*—David L. Lacey
*Assistant Examiner*—Thomas E. Daley
*Attorney, Agent, or Firm*—Oblon, Spivak, McClelland, Maier & Neustadt

[57] ABSTRACT

A method for measuring trace amounts of analyte substance(s), which utilize a pH electrode is disclosed. This method is by far simpler than conventional optical detecting systems. The apparatus for practicing the method is also disclosed. By the use of pH electrode, the apparatus is compact, inexpensive and easy to operate, and hence usable in small-size and medium-size hospitals or clinical laboratories and by patient's bedside.

6 Claims, 8 Drawing Sheets

METHOD AND APPARATUS FOR THE MEASUREMENT OF ANALYTE SUBSTANCES

BACKGROUND OF THE INVENTION

1. Field of the Invention

The present invention relates to a method for measuring analyte substance(s) and the apparatus therefor, and in particular to a method and apparatus suited for the quantitative immunoassay of specific substances contained in trace amounts in a multi-component solution such as specimens from biological sources and the apparatus therefor. While the present invention will hereinbelow be illustrated only for measurement of biosubstances in clinical examination, the method and apparatus of the present invention are applicable to a wide variety of fields such as pharmacy, biology, zoology, botany, agriculture and chemistry.

2. Description of the Prior Art

Substances participating in bioactivity of a living body are generally present in trace amounts, and still many of them play very important roles for the living body. The quantitative determination of such bioactive substances therefore is important in fields associated with living organisms, such as medical science and biochemistry. Various methods for that purpose have been proposed and put to practical use, among which a determination method of analytereceptor system utilizing enzymes, radioactive isotopes, chemiluminescent substances or the like as a label has been widely used. The analyte-receptor-type measurement comprises first contacting a solid phase having fixed a first receptor which can specifically bind an analyte which is the substance to be determined, with a sample solution and a labelled second receptor or a labelled analyte (hereinafter these labelled substances are referred to as "the conjugates") simultaneously or successively, thereby effecting an analyte-receptor reaction, washing the reaction mixture, and thereafter determining the amount of the conjugates remaining on the solid phase to measure the amount of the analyte in the sample solution. In this case substances having a large amplification effect such as radioisotopes and enzymes are used as the label. As regards the receptor, for an antigen or a hapten, an antibody which can specifically bind it is used; for an antibody, its antigen is used; for a DNA or RNA, another DNA or RNA complementary thereto is used; and for a ligand, its receptor is used. The heterogeneous EIA, so-called Enzyme Linked Immuno Sorbent Assay (ELISA) is known as a representative example of such determination.

In ELISA, a solid phase obtained by fixing a receptor capable of specifically binding the analyte to be determined, on a test tube, microplate or the like is used for capturing the substance to be determined in the sample solution. An enzyme is used as the label for signal amplification. For example where the analyte to be determined is an antigen, the sandwich-ELISA uses an enzyme-labelled second antibody (a second receptor) bindable to the antigen, and the competitive-ELISA uses an enzyme-labelled antigen as the conjugate. On the other hand, where the analyte to be determined is an antibody, the sandwich-ELISA uses an antigen as the receptor, and another antigen labelled with an enzyme as the second receptor. The competitive system utilizes an antigen as the receptor, selecting an antibody which competes with the antibody to be determined against the antigen, and labels the antibody thus selected with an enzyme. After being washed, the solid phase is contacted with a substrate solution for the above-mentioned enzyme used as the label and, if necessary, a chromophore, whereby the optical property of the system is changed with the proceeding of the decomposition reaction of the substrate, which change is then observed.

Several methods have been used for the purpose of observing the change of the optical property of the substrate solution. Among them, there are methods utilizing optical instruments such as optical absorption instruments fluorophotometer, and chemiluminescence photometer (see for example Ishikawa, Kawai and Miyai, ENZYME IMMUNOASSAYS, 1982, published from Igaku Shoin, Tokyo).

There is also a method which comprises comparing a substrate solution with a control solution and observing visually the difference in the color to judge the presence of a trace amount of an analyte substance (see for example Japanese Patent Application Laid-Open No. 128369/1985).

The above-mentioned optical measuring systems utilizing optical instruments, however, require expensive and large and complex equipment because they generally need a stable light source, a photometer having high sensitivity, a photomultiplier circuit with high precision, and the like. Further, specialized technicians must attend to the measurement since special technique is required for the measurement.

On the other hand, the direct visual observation method is a qualitative one. It is liable to personal variation in judgement of color change and to the observer's subject. Further, judgement itself is sometimes difficult for measurement of an extreme trace substance where the color change is very small.

SUMMARY OF THE INVENTION

Accordingly, an object of the present invention is to provide a method for the measurement of an analyte substance(s) in a sample by measuring the decomposition reaction of a substrate solution objectively and with high detection accuracy, with the method being free from the indefiniteness of judgement which depends on the observer's subject; and the apparatus therefor.

Another object of the present invention is to provide a method for the measurement of an analyte substance(s), which has a measurement system which is far simpler from the optical measurement systems, and the apparatus therefor.

Still another object of the present invention is to provide an apparatus for measuring analyte substances, which can be operated by an untrained operator or which is suited for use, when a quick decision is required for diagnosis, by a person in charge of medical care or of other medical field.

Yet another object of the present invention is to provide a compact and inexpensive apparatus for measuring analyte substances, which can be used in hospitals of small or medium size, clinical laboratories or at a patient's bed side.

The measurement method of the present invention comprises contacting a solid phase having the product of a completed analyte-receptor reaction with a substrate solution. It utilizes the pH change of the substrate solution due to the advance of a decomposition reaction of the substrate as it reacts with the solid phase. It is further characterized by providing the solid phase in a spaced relationship with and facing a pH sensitive surface of a pH electrode such that the slit distance between the solid phase and the pH sensitive surface is not more than 1 mm. The pH change of the substrate solution enclosed in the slit is measured to perform the assay.

Further, the measurement apparatus of the present invention is an apparatus for measuring analyte substances by contacting a solid phase having the product of a completed analyte-receptor reaction with a substrate solution and utilizing the pH change of said substrate solution with the advance of decomposition reaction of the substrate solution. The apparatus comprises:

a) a cell having an inlet and an outlet for the substrate solution, b) a pH electrode housed in the cell, c) a pump for supplying the substrate solution into the cell, d) a means for introducing into the cell, a solid phase having fixed thereon a first receptor capable of specifically binding the analyte to be measured and which has been contacted with a sample solution and a labelled second receptor or labelled analyte and then washed, and e) a means for positioning the solid phase, which can adjust the position of the solid phase introduced into the cell to a position facing and in a spaced relationship with the pH sensitive surface of the pH electrode such that the slit distance between the two is not more than 1 mm.

In the measurement method of the present invention, as illustrated in FIG. 1, solid phase 3 having completed analyte-receptor reaction and been washed, and having analyte-receptor complex 5 containing the conjugate absorbed on the solid phase is positioned facing and in a spaced relationship with the pH sensitive surface 2 of the pH electrode 1 such that the distance, d, of the slit therebetween is not more than 1 mm. This distance can be decrease until it approaches to the depth of electrochemical double layer, which is usually less than 100 nm. The pH change with the advance of decomposition reaction of a substrate solution 4 which is substantially enclosed in the narrow slit is then directly measured.

Conventional measurement apparatus of analyte-receptor systems utilizing a pH electrode as a detecting means have not been thought practical since their detection sensitivity is by far inferior to that of systems utilizing an absorptiometer or fluoro photometer. The present inventors, however, found that, unexpectedly, a high detection sensitivity of the same degree as that of the conventional optical systems can be obtained by setting the distance between the pH sensitive surface of the pH electrode and the solid phase having completed analyte-receptor reaction at not more than 1 mm.

The fundamental procedure for the present method is:

(1) prepare a solid phase 3 having a receptor-fixed surface;

(2) have the solid phase react with an analyte solution and a conjugate solution to form an analyte-receptor complex (containing the conjugate) 5 on the surface of the solid phase;

(3) wash the solid phase to eliminate free analyte and free conjugate;

(4) position the surface of the solid phase at a distance of not more than 1 mm from the pH sensitive surface 2 of a pH electrode 1;

(5) prior to or after step (4), introduce a substrate solution at least into the slit zone between the solid phase and the pH sensitive surface of the pH electrode; and (6) have the substrate solution decompose by action of the conjugate 5 adsorbed on the surface of the solid phase, and measure the resulting change in pH of the substrate solution with the pH electrode.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENT

Hereinbelow a preferred embodiment of the invention will be described with reference to the drawings. Though the embodiment utilizes as the solid phase a cylindrical tube having a small diameter as an example, it is to be understood that the apparatus of the following embodiment is not limiting of the invention.

Figure 1:
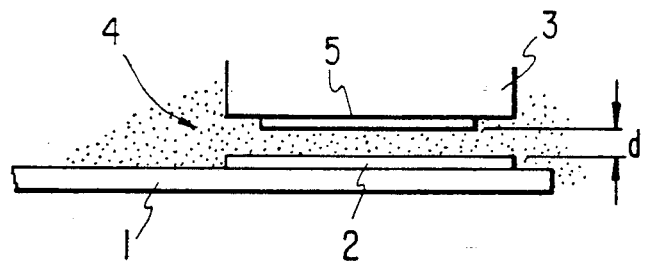
FIG. 1 is a cross-sectional view showing the principle of the measurement method and apparatus according to the present invention.
Figure 2:
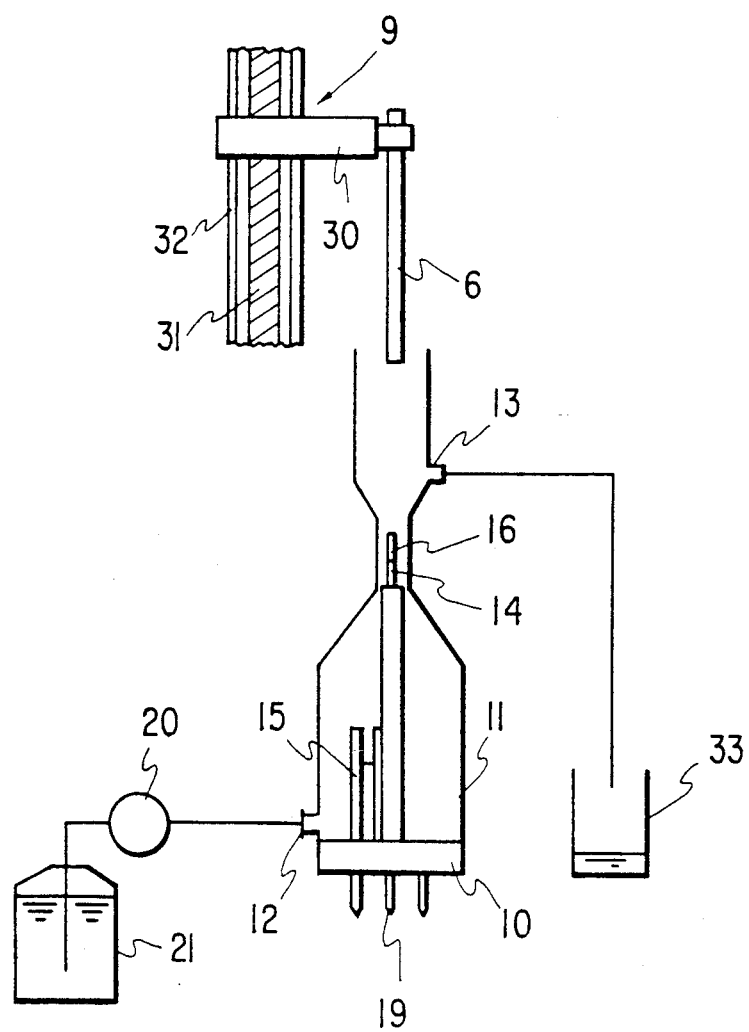
FIG. 2 is a schematic view of the measurement apparatus of the present invention.

FIG. 2 is a cross-sectional view of the measurement apparatus of the present invention. The apparatus comprises a cell 11 equipped with an inlet 12 and an outlet 13 for a substrate solution, a pH electrode 14 and a reference electrode 15 disposed in the cell 11, a pump 20 for feeding the substrate solution into the cell, a means 9 for introducing into the cell 11 a small-diameter tube 6 having fixed on the inner wall thereof a receptor, and a positioning means (not shown) for setting the distance between the inner wall surface of the tube and the pH sensitive surface 16 of the pH electrode 14 at not more than 1 mm. 21 is a reservoir for the substrate solution.

The cell 11 has cylindrical large-diameter sections at its upper and lower parts and a cylindrical small-diameter section at the middle part, the both ends of the large-diameter sections being open. The inlet 12 for the substrate solution is mounted on the lower large-diameter section, and the outlet 13 for the substrate solution on the upper large-diameter section. The bottom opening of the cell is sealed With a cap 10 made of an insulating resin for housing in the cell the pH electrode 14 and the reference electrode 15. The cell itself may be made of a plastic, inorganic glass or a metal. Connector 19 which connects the pH electrode and the reference electrode to an electric circuit (not shown) for operating the pH electrodes and reading.

As the pH electrode 14 to be disposed in the cell 11 use is made of, in addition to so-called glass electrodes which have been most widely used, various micro pH electrodes, e.g. a pH sensitive field-effect transistor (hereinafter referred to as "pH-FET"), surface oxidized metal-type electrodes such as palladium oxide/palladium wire, coated wire-type pH electrodes obtained by coating metal wire or carbon wire with a pH sensitive polymer film made of polyvinyl chloride containing a proton receptor. However, electrodes other than pH-FET have some problems as described below.

Glass pH electodes having a small diameter tend to suffer an increase in induction noise; surface oxidized metal-type pH electrodes are readily available in small diameters but have problems in life when immersed in water for a long period; and coated wire-type pH electrodes have, though also readily available in small diameters, drawbacks of narrow linear response range and short life in water.

Figure 3:
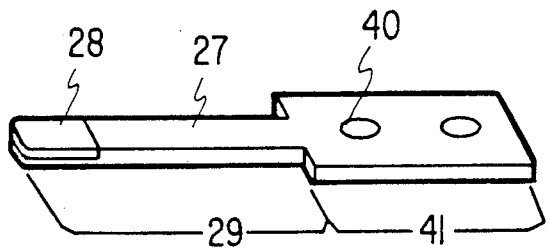
FIG. 3 is a perspective view of a pH-FET.

On the other hand, pH-FET has the following excellent characteristics and is hence most suited for use in the apparatus of the present invention: (1) small-diameter type is readily obtainable; (2) small induction noise even when made into small-diameter type; (3) it is manufactured by IC technology, whereby the variation in characteristics is small and the pH sensitive surface (gate) can be made minutely; (4) it responds quite quickly to a pH change, while allowing no hysteresis to remain in the response curve; (5) wide linear response range corresponding to pH changes; (6) almost infinite life and only a small change in characteristics such as pH sensitivity with time when stored in water; and so forth. Several types of pH-FET are known including: (i) all-around insulated type (see Japanese Patent Publication No. 43863/1982), (ii) pn-junction-isolation type (see Japanese Utility Model Publication No. 5245/1983); (iii) SOS type (see Japanese Patent Application Laid-Open No. 48646/1984) and the like. Any of such pH-FET device can be used in the present invention as long as it has the following fundadmental structure as shown in FIG. 3:

(1) a pH sensitive surface (gate) 28 is provided on tip 29 of the device, (2) tip 29 is of a size capable of being inserted into a small-diameter tube for fixing receptor, (3) the length of tip 29 is 1 to 10 mm, preferably 1 to 3, mm, and (4) all the surfaces, i.e. top, bottom and side surfaces, are electrically insulated against the surrounding solution.

A bonding pad 40 for lead wire is provided on the tail part 41 of the pH-FET device, no limitation being on the shape of the tail part.

As to the size of the pH-FET device tip, it is preferably such that can allow the tip to get into a small-diameter tube for fixing receptor having generally an inner diameter of not more than 0.8 mm. Thus, for example for a small-diameter tube having an inner diameter of 0.53 mm, an device tip having a width of not more than 0.45 mm and a thickness of not more than 0.20 mm may be sufficient. As to the length of the device tip, if it is larger than 10 mm, the tip will cause ready breakage, require a large length of a receptor-fixed portion of the small-diameter tube. If the length is less than 1 mm the length of the tip inserted into the small-diameter tube will be too short, rendering the enzyme reaction in the tube susceptible to the solution outside of the tube, which is not preferred. The device tip, as it is, must be electrically insulated against the surrounding solution. In the above-mentioned pH-FET of the all-around insulated type, the entire circumpherence of the device tip is insulated with a layer of silicon dioxide, silicon nitride or the like. In the pH-FET of junctionisolation type, electrical insulation is achieved by pn junction (see Tsutsumi, SENSOR TECHNOLOGY, May, 1986, extra issue). Further in the pH-FET of SOS type, the bottom surface of the device is insulated with a saphire base plate and the top and side surfaces with a layer of silicon nitride or the like.

It is preferred that the pH-FET used in the invention have a pH sensitivity at 25° C. of 40 to 60 mV/pH, more preferably 50 to 60 mV/pH. The pH sensitive membrane is preferably made of substances having high stability in water, such as silicon nitride, aluminum oxide and tantalum oxide, among which tantalum oxide and aluminum oxide are preferred in terms of in-water stability, pH-responding characteristics and the like. PH-FET's with the pH-sensitive membrane of tantalum oxide are most suited for the pH electrode used in the present invention.

It is preferred that the pH-FET employed have an extremely low noise level (generally not more than 0.05 mV at a constant pH). To this end, its mutual conductance is preferably at least 50 $\mu\Omega$, more preferably at least 100 $\mu\Omega$, and most preferably at least 150 $\mu\Omega$. The leakage current produced when a voltage of 3V is applied between the element tip of the pH-FET and an external electrode both of which are immersed in a physiological saline solution is preferably not more than 30 nA, more preferably not more than 10 nA. If the mutual conductance is less than 50 $\mu\Omega$ or the above-defined leakage current is more than 30 nA, a large noise will be generated in the course of the measurement.

As the reference electrode 15, use is made of liquid-junction type reference electrodes such as saturated calomel electrode and silver-silver chloride electrode, field-effect transistors comprising a gate of ion-insensitive membrane (see Japanese Patent Publication No. 25221/1983), or coatedwire reference electrodes comprising metal wire or carbon wire coated with an ion-insensitive membrane, among which, at this moment, liquid-junction reference electrodes are preferred in view of their high reliability. Such reference electrode is preferably mounted, as shown in FIG. 2, inside the large-diameter bottom section of the cell where it can form liquid junction with the pH-sensitive surface of the pH electrode. The reference electrode can also be placed at an optional position outside the cell which forms liquid junction with, the cell.

The means 9 for introducing the small-diameter tube 6 into the cell, introduction of the tube into the cell by simply holding it with the hand may work. Also available is, for example, a system shown in FIG. 2 which comprises a holding element 30, the tip of which holds the small-diameter tube 6, and a screw 31 inserted perpendicular through the other end of the holding element 30. Rotation of the screw 31 driven by a stepping motor (not shown) moves the holding element upward or downward automatically. In FIG. 2, 32 is a guide fitted parallel with screw 31. Other known mechanisms can also be employed for moving upward and downward the holding element 30.

Known mechanisms can be employed as the positioning means for the small-diameter tube 6, which adjust the slit distance between the inner Wall surface of the tube and the pH-sensitive surface 16 of the pH electrode 14. For example, the small-diameter section of the cell 11 can work as a guide for the tube by making the inner diameter of the small-diameter section a little larger than the outer diameter of the tube. By the use of the above-mentioned positioning means for the small-diameter tube, the distance between the inner wall surface of the small-diameter tube 6 and the pH sensitive surface of the pH electrode is set at not more than 1.0 mm, preferably not more than 0.5 mm. If the distance exceeds 1.0 mm, the rate of pH change of the substrate solution will be rapidly decreased, rendering high detection sensitivity practically impossible to achieve.

Figure 4:
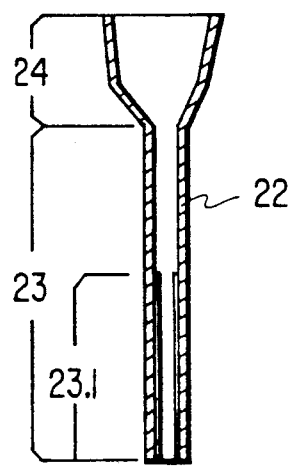
FIGS. 4 and 5 are cross-sectional views showing examples of a small-diameter tube.
Figure 5:
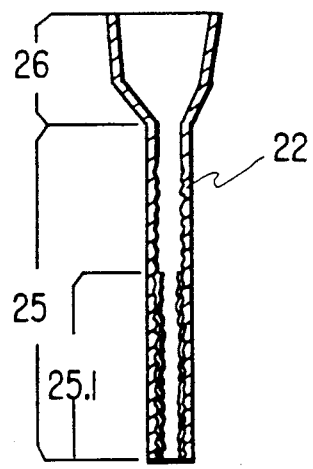

The small-diameter tube 67 must be of a length sufficiently log for introducing the pH sensitive surface of the pH electrode fully thereinto. Thus, for example for a pH electrode with a pH sensitive surface having a length of 1.5 mm, the receptor-fixing portion of the small-diameter tube is generally of a length of at least 3 mm. The small-diameter tube may have any shape as long as its receptor-fixing portion satisfies the above condition. One example of the tube is shown in FIG. 4, wherein the small-diameter tube 22 is of a pipet-tip shape and comprises a small-diameter part 23 and a large-diameter part 24. The large-diameter part provides a taper for receiving a pipettor, and a receptor being fixed onto the inner wall 23-1 of the end of the small-diameter part 23. FIG. 5 shows another example of the small-diameter tube. Here, the small-diameter tube 22 is also of a pipet-tip shape, and comprises projections and concave regions on inner wall 25 of the small-diameter part, thereby enlarging its surface area. On the end part 25-1 the receptor is fixed. The large-diameter part serves as a taper for receiving a pipettor in the same manner as in FIG. 4. Such enlargement of the surface area of the inner wall of the small-diameter tube can increase the detection sensitivity and shorten the incubation period.

Examples of materials which can be used for the small-diameter tube include, among others, polyolefins such as polystyrene, polyethylene, polypropylene, polytetrafluoroethylene, polyvinyl chloride, polymethyl methacrylate, polyvinyl alcohol and ethylene-vinyl alcohol copolymers; polyesters such as polyethylene terephthalate and polybutylene terephthalate; polysiloxanes such as polydimethylsiloxane; polyamides such as 6-nylon and 6,6-nylon; polycarbonates; cellulose-related polymers such as cellulose acetate and nitrocellulose; and various inorganic glasses.

Table 1 shows a list correlating examples of substances fixed as a receptor on such a small-diameter tube, with the items to be measured.

TABLE 1

| Substance to be fixed on small-diameter tube | Item to be measured |
| --- | --- |
| Anti-AFP antibody | AFP |
| Anti-CEA antibody | CEA |
| Anti-ferritin antibody | ferritin |
| Anit-$\beta_2$ microglobulin antibody | $\beta_2$ microglobulin |
| Anti-IgE antibody | IgE |
| Anti-IgG antibody | IgG |
| Anti-TSH antibody | TSH |
| Anti-HCG antibody | HCG |

TABLE 1-continued

| Substance to be fixed on small-diameter tube | Item to be measured |
| --- | --- |
| Anti-insulin antibody | insulin |
| Anti-HBs antibody | HBs |
| Anti-HBe antibody | HBe |
| HBs antigen | anti-HBs antibody |
| Anti-$C_1$ q antibody | immuno complex |
| dsDNA | Anti-dsDNA antibody |
| Insulin receptor | insulin |
| DNA | complementary DNA |

As to the combination of a labelling enzyme for the conjugate and a substrate solution in the present invention, it is necessary to use one which causes a large change in the pH of the substrate solution due to enzyme reaction. Examples of such combination include combinations of hydrolysis enzymes and their substrates such as triacylglycerol lipase/triacylglycerol, acetylesterase/acetic acid ester, acetylchloline esterase/acetylcholine, gluconolactonase/gluconolactone, alkaliphosphotase/p-nitrophenol phosphoric acid, allylsulfatase-/allylsulphate, urease/urea and barbiturase/barbiturate; combinations of redox enzymes and their substrates such as glucose oxidase/glucose, choline oxidase/choline and catechol-1,2-dioxygenase/catechol; and the like. Among the above, the combinations of urease/urea, triacylglycerol lipase/triacylglycerol and glucose oxidase/glucose are suited for practical use because of availability of the stable and highly active enzymes and availability of inexpensive and highly purified substrate solution. Particularly preferred is the combination of urease/urea on account of its large pH change with the advance of enzyme reaction.

Now described is the measurement procedure with the apparatus of the present invention for the case of antigen measurement by a 1-step sandwich method. The competitive method or 2-step sandwich method uses, though somewhat different in procedures, the same apparatus construction, and hence explanations thereon are omitted herein. First a receptor is fixed on the inner wall surface of a small-diameter tube 6. Conventional methods utilized in ELISA are applicable hereto. For example, when the receptor is fixed by physical adsorption, first the small-diameter tube is washed thoroughly, a buffer solution of a first antibody as a receptor is introduced into the small-diameter tube, and the tube with the contents is allowed to stand still at 0° C. to 40° C. for a specified time. At this time only the tip of the small-diameter tube may be immersed in the receptor solution. In this case the receptor is adsorbed onto the outer wall as well as onto the inner wall of the tip of the small-diameter tube, which fact does not adversely affect the measurement. The small-diameter tube is then washed with a buffer solution, and thereafter subjected to blocking treatment. The blocking is conducted by treating the washed small-diameter tube with, for example, bovine serum albumin, calf serum albumin, serums of various cattles, various immunoglobulins, surfactants or the like. It is necessary to conduct the blocking not only on the receptor-fixed portion but on all the rest of the parts where a contact with sample solution or conjugate solution may occur.

Next, the tip of the small-diameter tube, after the blocking treatment, is immersed in the sample solution containing a prescribed amount of a labelled second antibody, followed by incubation for a prescribed time. By this procedure a sandwich-type antigen-antibody complex of first antibody-antigen-labelled second antibody is formed on the inner wall of the small-diameter tube.

Then, by washing, free antigen to be measured, free labelled second antibody had free complex of antigen-labelled second antibody which have not participated in forming the above sandwich are removed from the inner wall surface of the small-diameter tube. By the incubation and washing procedure there is fixed n the inner wall surface of the small-diameter tube a sandwich-type antigen-antibody complex containing the labelling enzyme in an amount corresponding to the concentration of the antigen to be measured in the sample solution.

Figure 6:
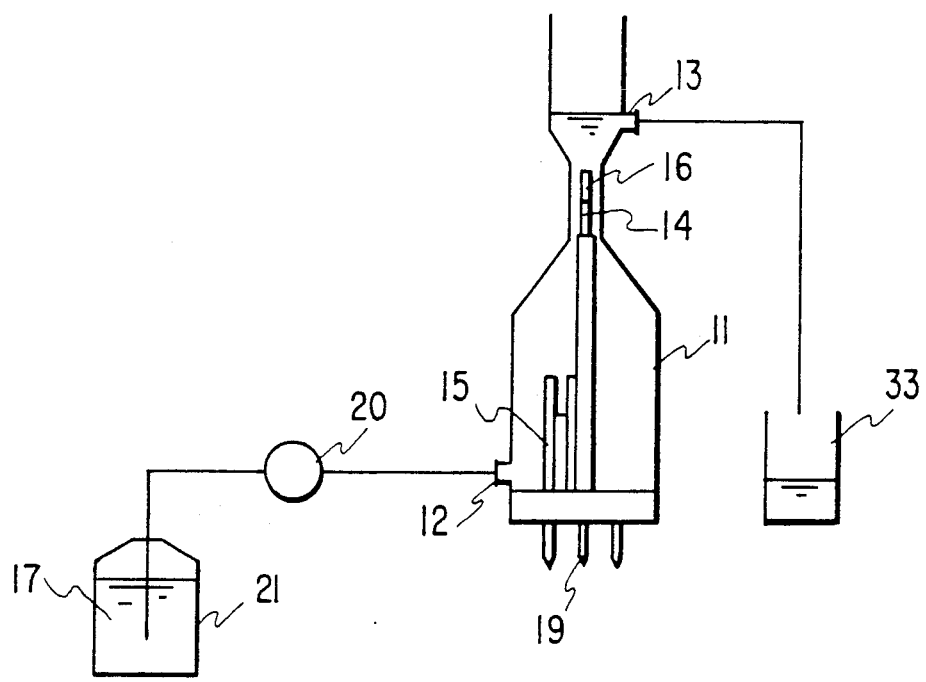
FIGS. 6 and 7 are schematic views showing the measurement method with the apparatus of the present invention.

On the other hand, in the cell, as shown in FIG. 6, the substrate solution 17 is fed by pump 20 from a reservoir 21 into the cell, and overflown from the outlet 13, thereby washing the pH sensitive surface 16 of the pH electrode 14 and the reference electrode 15. The liquid level in the cell is above the tip of the pH sensitive surface of the pH electrode. 33 indicates a reservoir for effluent.

Figure 7:
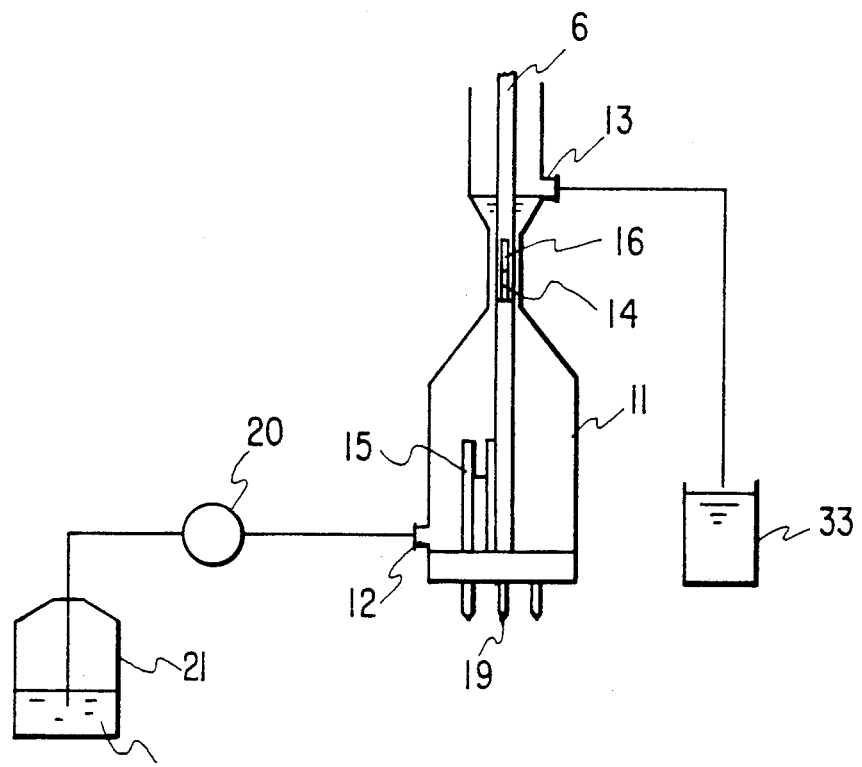
Figure 8:
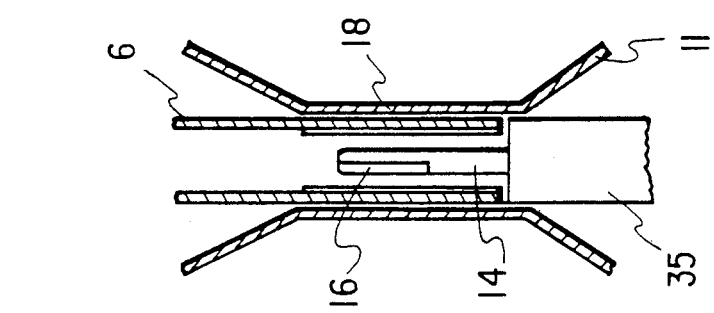
FIG. 8 is an enlarged cross-sectional view of the small-diameter section of the cell.

The enzyme reaction is started by, as shown in FIG. 7, inserting into the cell the small-diameter tube 6 after incubation and washing, from the top opening of the cell using a means for introducing small-diameter tube (not shown), such that the small-diameter tube will wholly enclose the pH sensitive surface of the pH electrode. During the above procedure, the feed pump 20 is preferably stopped. FIG. 8 shows a detail of the small-diameter section of the cell and its vicinity with the small-diameter tube 6 being introduced into the cell 11. Then, the decomposition reaction of the substrate proceeds in the small-diameter tube, and the pH change with the advance of the reaction is measured. From the rate of change of the pH, the enzyme activity on the labelled second antibody, that is, the concentration of the antigen in the sample solution is measured.

What is important, when the small-diameter tube 6 is inserted into the cell, is that the bottom end of the small-diameter tube 6 is, as shown in FIG. 8, placed as close to the tip of the resin part 35 of the pH electrode as possible. It is preferred that, when the enzyme activity is determined, the substrate solutions outside and inside the small-diameter tube not be mixed with each other. To this end, the resin part 35, the outer diameter of which has been set approximately the same as that of the small-diameter tube 6, is fixed inside the small-diameter section 18 of the cell. Then when the enzyme activity is measured, the small-diameter tube 6 is inserted downward from the top to a position where its tip touch the resin part 35. By this procedure, the bottom opening of the small-diameter tube 6 is clogged appropriately with the resin part 35 of the pH electrode 14, thereby isolating the substrate solution in the small-diameter tube. In this case it is necessary that the pH sensitive surface 16 of the pH electrode keep an electrical liquid junction with the reference electrode 15, which can generally sufficiently be assured through minute clearances resulting from minute projections and concave sections on the top surface of the resin part 35 and the bottom end of the small-diameter tube 6.

Other features of the invention will become apparent in the course of the following descriptions of exemplary embodiments which are given for illustration of the invention and are not intended to be limiting thereof.

EXAMPLE 1

Human-IgG was measured by using an ELISA apparatus comprising a small-diameter tube as a solid phase and pH-FET as a detecting means.

Fabrication of ELISA Apparatus

A cell shown in FIG. 2 was used. As the pH electrode 14, was used an all-around insulated pH-FET manufactured according to a process described in Japanese Patent Publication 43863/1982, on the gate of which had been vapor-deposited tantalum oxide as pH sensitive membrane. The pH-FET had an overall size of 5.5 mm long, 0.45 mm wide and 0.15 mm thick, and was provided with a gate (pH sensitive surface) extending 0.8 mm down from the tip thereof. The pH-FET was fixed with a resin 35 such that the tip of 1.5 mm long containing the gate was exposed out of the resin part. The resin part had an outer diameter of 0.60 mm. The clearances between the pH sensitive surface of the pH-FET and the inner surface of the small-diameter tube had an maximum, d, of $(0.53-0.15)/2=0.19$ mm. The inner diameter and the length of the small-diameter section of the reaction cell were 0.65 mm and 15 mm respectively. A liquid-junction type reference electrode 15 of silver/silver chloride was used. A pump 20 of the Perista-type was used and the flow rate was set at 1 ml/min.

The pH sensitivity and the mutual conductance of the pH-FET used was 57.3 mV/pH at 37° C. and 380 $\mu\Omega$ respectively. The pH-FET was operated by coupling it to a constant-current circuit with a drain voltage of 4 volts and a drain current of 100 $\mu$A. As to the output signal of the pH-FET, a potential of the source current based on the liquid-junction reference electrode (hereinafter referred to as "source potential") was measured and recorded.

Fixation of Receptor Antibody on the Small-Diameter Tube

Anti-human-IgG (sheep) was selected as a receptor and fixed on a small-diameter tube according to the following procedure. As the small diameter tube was used a cannula (commercial name: Happycas Z) shown in FIG. 4 made of polytetrafluoroethylene by Medikit Co. having an inner diameter of its small-diameter portion of 0.53 mm. The small-diameter portion of the cannula had a length of 25 mm and the large-diameter portion had an inner and outer diameters and a length of 4 mm, 6 mm and 20 mm, respectively. A 50 $\mu$g/mlPBS solution (pH: 7.0) of anti-human-IgG was prepared, and in the tip of 10 mm long of the above cannula was immersed in the solution at 4° C. for 24 hours, whereby the anti-human-IgG was physically absorbed on the inner and outer walls thereof. The inner and outer walls of the cannula having thus adsorbed the anti-human-IgG were then washed well with a PBS solution, (pH: 7.0) containing 0.05% of a surfactant (commercial name "Tween 20"). After being washed, the inner and outer walls of the entire small-diameter portion of the cannula was immersed in a PBS solution containing 1% bovine serum albumin (BSA) and 0.05% Tween-20 at a room temperature for one hour, thus subjected to blocking treatment.

Preparation of Enzyme-Labelled Antibody

Urease separated from soy-bean and purified (Type C-3, available from Sigma Co.) was used as a labelling enzyme, and made to bind anti-human-IgG (goat) by the avidin-biotin method as follows. First, a 0.1 M sodium bicarbonate buffer solution (pH: 8.3) containing 1 mg/ml urease and 1 mM EDTA was prepared. Separately, a 1 mg/ml solution of biotin-N-hydroxysuccimide in DMSO was prepared. Then 1 ml of the urease solution was reacted with 5 μl the biotin-N-hydroxysuccimide solution at a room temperature for 4 hours to add biotin to the urease. After the reaction, the reaction mixture was subjected to gel chromatography with pD-column (available from Pharmacia Co.) to give a fraction of biotinurease. The thus obtained fraction was diluted with a PBS solution containing 1% BSA, 0.05% Tween-20, 1 mM EDTA and 0.01% $NaN_3$ (pH: 4; hereinafter this solution is frequently used and will hence be referred to as "ciluting buffer") to give a 25 μg/ml solution.

Separately, avidin-D (Vector Co.) and biotin-antihuman-IgG (Tago Co.) were diluted with the same diluting buffer to give solutions of 7.6 μg/ml and 6.9 μg/ml respectively. The thus obtained solutions of biotin-urease, adivin-D and biotin-antihuman-IgG were mixed at a volume ratio of 1:1:1 to give the desired solution of urease-labelled anti-human-IgG. Hereinafter this solution is referred to as "the conjugate solution".

Preparation of Calibration Curve for Human-IgG

Prepared next was an calibration curve for human-IgG, to test the Performance of the ELISA apparatus of the present invention. First, a prescribed amount of human-IgG was dissolved in the above-described diluting buffer to give a human-IgG solution. Then the thus obtained human-IgG solution was mixed with the same volume of the above prepared conjugate solution. In the meantime, the small-diameter tube having fixed the antihuman-IgG was pulled out from the blocking solution and washed with a PBS-Tween-20 solution. The above-described mixed solution of the human-IgG-conjugate was introduced into the small-diameter tube and then incubated at a room temperature for 30 minutes, followed by washing with a PBS-Tween-20 solution.

Figure 9:
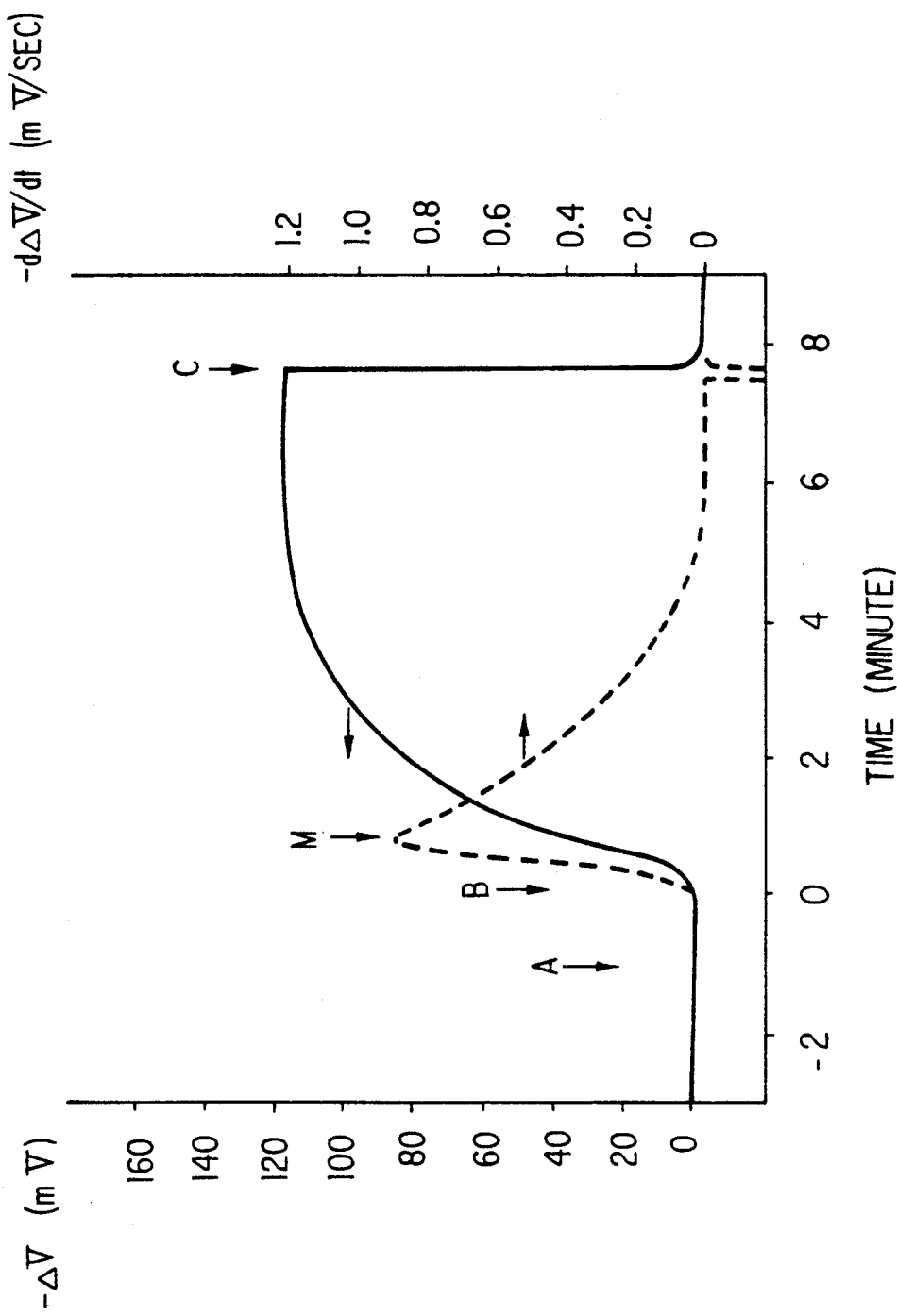
FIG. 9 is a graph showing the change with time of the source potential and its changing rate of the pH-FET.

A substrate solution of 0.1 M urea, 1 mM ammonium chloride and 0.15 M sodium chloride was prepared and the solution was charged to a reservoir 21 shown in FIG. 2. Then the pump 20 was operated to feed the substrate solution into the cell 11 and overflow it from the cell outlet 13. From this time on the source potential of the pH-FET and its changing rate were recorded. An example of the recording is shown in FIG. 9. In FIG. 9, $\Delta V$ is the changing rate of the source potential with the advance of reaction based on the source potential against the substrate solution before the start of the reaction and is shown in full line. $d\Delta V/dt$ is its time differential and shown in dotted line. The pump 20 was stopped at time A in FIG. 9. At time B, above-described small-diameter tube after the incubation-washing was inserted into the small-diameter section of the cell as shown in FIG. 7. Let the time of the insertion be 0 (zero). Immediately thereafter, in the small-diameter tube the decomposition reaction of urea into ammonia and carbon dioxide started, and the pH of the substrate solution changed to alkaline side, or to decreasing the source potential. In the course of the reaction, the changing rate of $\Delta V$ reached its maximum at time M. At time C, the small-diameter tube was pulled out from the cell and, at the same time, the feed pump was started, whereby the source potential and its time differential returned to the original values at once.

Figure 10:
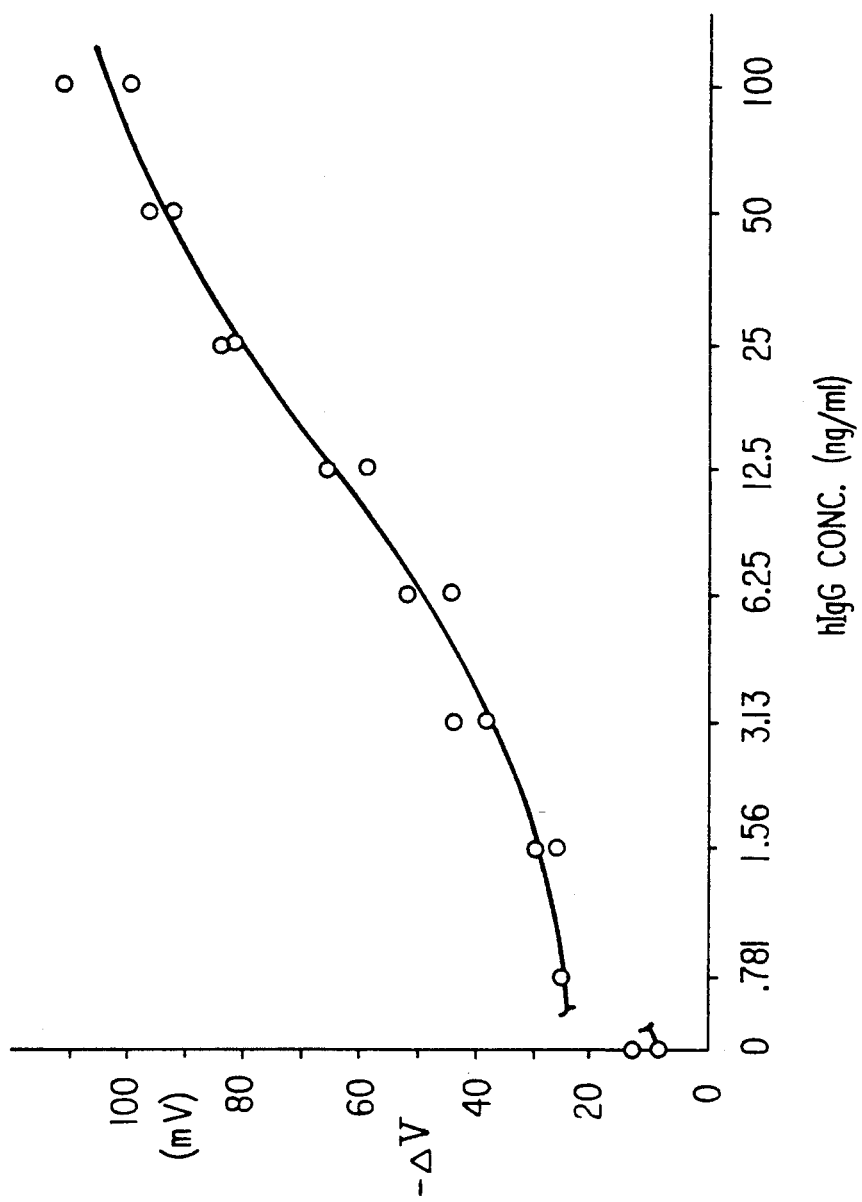
FIGS. 10, 11 and 13 are graphs showing the relationships between the concentration of analyte and the pH response curve.
Figure 11:
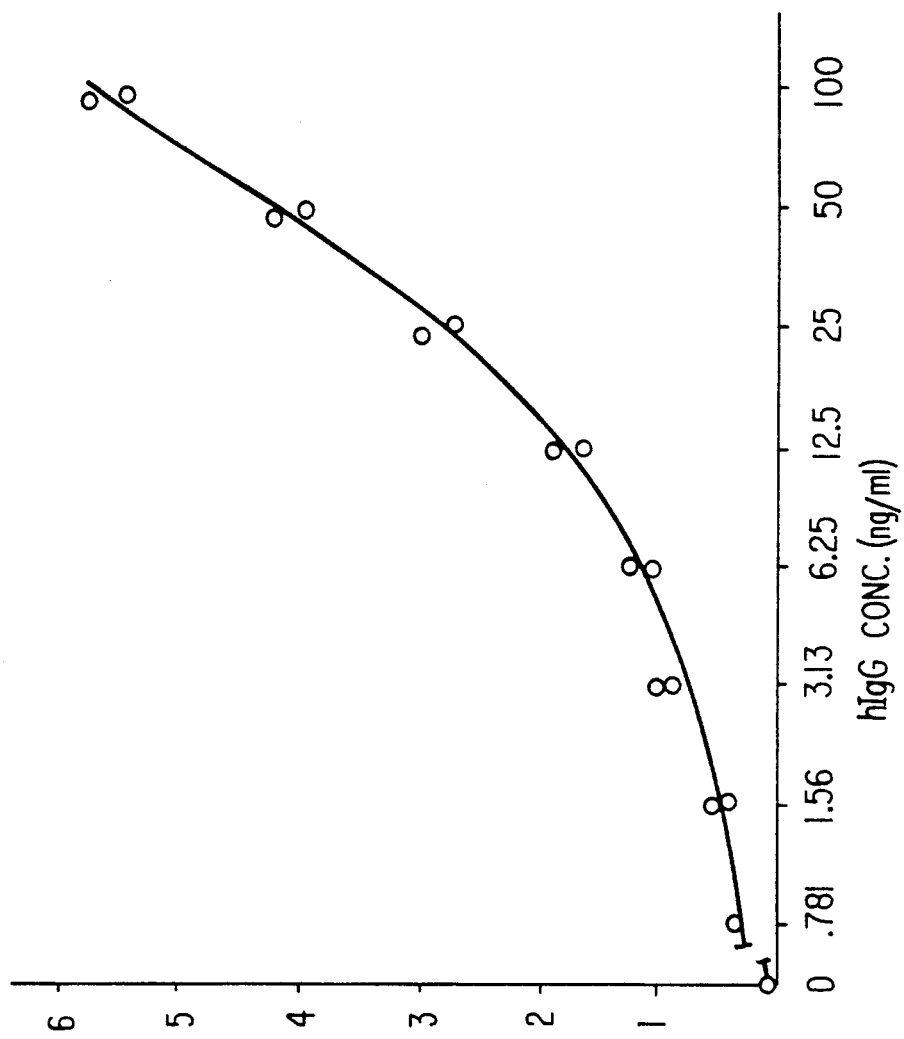

Following the above procedures, pH response curves were determined for to human-IgG solutions of various concentrations, and from the results thereof two calibration curves shown in FIGS. 10 and 11 were drawn. FIG. 10 shows the relationship between and the concentration of the human-IgG and $\Delta V$ at 5 minutes after the insertion of the small-diameter tube. FIG. 11 shows the relationship between the maximum value of $d\Delta V/dt$ ($d\Delta V/dt$ at time M in FIG. 9; so-called peak rate) and the concentration of the human-IgG. In both of the calibration curves of FIGS. 10 and 11, the lower detection limit of the concentration is about 1 ng/ml. When FIG. 10 is compared with FIG. 11, while $\Delta V$ gets, at about 100 ng/ml, near to a saturation in FIG. 10, it shows no such tendency in FIG. 11. This fact suggests that a wider range of determination with a single calibration curve may be obtained by employing the so-called peak rate than by employing $\Delta V$ at 5 minutes after the insertion of the small-diameter tube.

EXAMPLES 2 THROUGH 8 AND COMPARATIVE EXAMPLES 1 THROUGH 3

Figure 12:
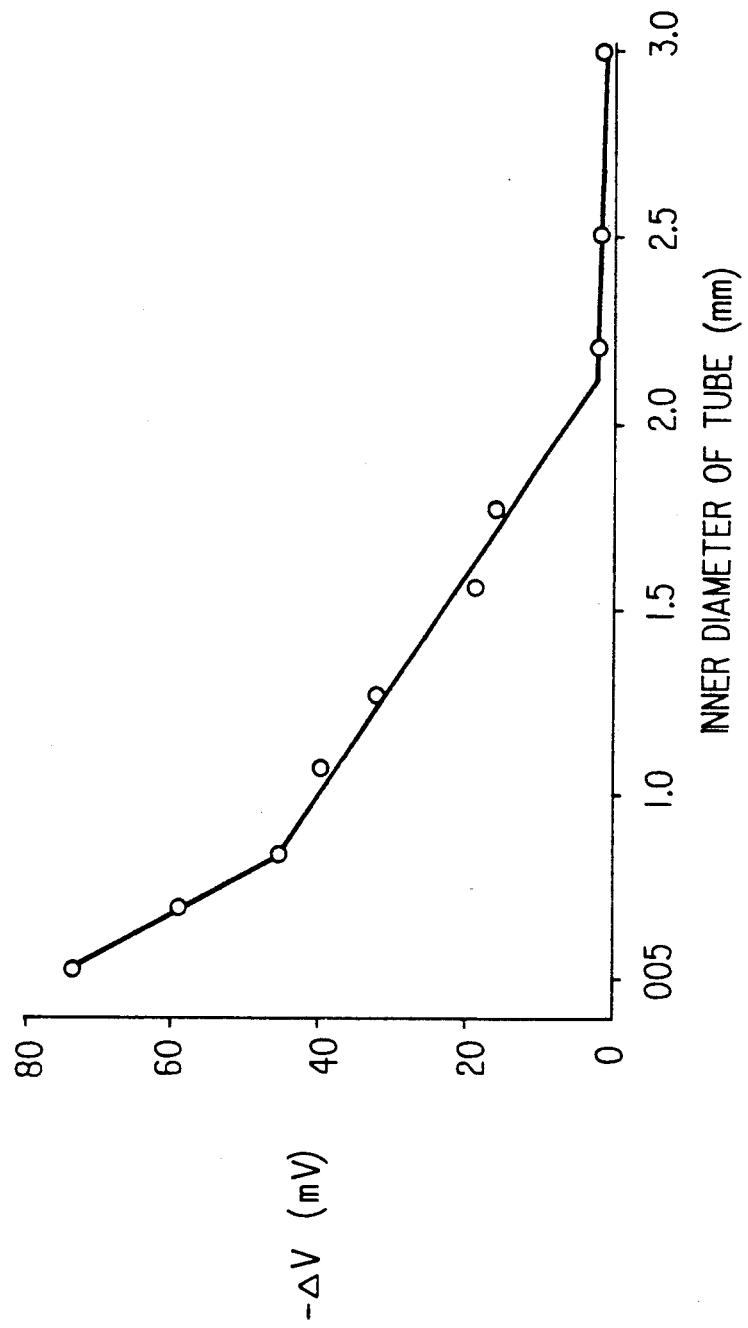
FIG. 12 is a graph showing the relationship between the distance of the pH sensitive surface from the inner wall surface of the small-diameter tube and the source potential.

Example 1 was repeated except for changing the inner diameter of the small-diameter tube for fixing the receptor in a range of from 0.53 to 3.0 mm, to study the change of the pH response curve. For this purpose, ELISA was conducted by using cells having various inner diameters, L, and the resin parts having various diameters, a, and a receptorfixing small-diameter tube having an outer and an inner diameters, $l_1$ and $l_2$ respectively, while the following relationships were maintained among the sizes: L−a=0.05 mm, a=$l_1$ and $l_1$ - $l_2$=0.16 mm. Here the maximum, d, of the clearance between the pH sensitive surface of the pH-FET and the inner surface of the small-diameter tube is represented by: d=($l_2$−0.15)/2.

pH response curves were obtained with the above reaction cells and small-diameter tubes in the same manner as in Example 1 on a 10 ng/ml human IgG solution which was the objective solution to be determined. From the results obtained the relationship between the inner diameter of the receptor-fixing small-diameter tube and the output of pH-FET at 5 minutes after the start of the enzyme reaction was determined and shown in Table 2 and FIG. 12. Table 2 also shows the clearances, d's, between the pH-FET sensitive surface and the inner wall surface of the small-diameter tube. As is clear from FIG. 12, the smaller the inner diameter of the small-diameter tube, the larger the output of the pH-FET for the same human-IgG concentration. Where the inner diameter of the small-diameter tube is at least 2.20 mm, that is, the clearance, d, is at least 1.0 mm, no appreciable pH change is noted at a reaction time of about 5 minutes. Where the inner diameter of the small-diameter tube is less than 2.2 mm, there can be obtained an output sufficient to be detected, which ranges from several mV to several tens of mV. Further, where the inner diameter is 0.8 mm or less, that is, the clearance, d, is less than 0.20 mm, an output of as large as at least 45 mV can be obtained.

TABLE 2

| | Inner diameter of small-dia. tube (mm) | Clearance d (mm) | Output of pH-FET after 5 minutes (mV) |
|---|---|---|---|
| Example 2 | 0.53 | 0.19 | 73.5 |
| Example 3 | 0.70 | 0.28 | 58.5 |
| Example 4 | 0.83 | 0.34 | 45.4 |
| Example 5 | 1.08 | 0.47 | 39.5 |

TABLE 2-continued

| | Inner diameter of small-dia. tube (mm) | Clearance d (mm) | Output of pH-FET after 5 minutes (mV) |
|---|---|---|---|
| Example 6 | 1.26 | 0.56 | 32.0 |
| Example 7 | 1.56 | 0.71 | 19.2 |
| Example 8 | 1.77 | 0.81 | 15.8 |
| Comp. Ex. 1 | 2.20 | 1.03 | 2.0 |
| Comp. Ex. 2 | 2.50 | 1.18 | 1.8 |
| Comp. Ex. 3 | 3.00 | 1.43 | 1.2 |

EXAMPLE 9

Alpha-fetoprotein was measured by using a small-diameter tube as a solid phase and pH-FET as a detecting means as in Example 1.

Anti-AFP polyclonal antibody (Dako) was adsorbed on a polytetrafluoroethylene cannula from 50 μg/ml PBS solution (pH: 7.0) as in Example 1. Washing and blocking were carried out through the same procedure as in Example 1.

Anti-AFP monoclonal antibody (Nippon Viotest Laboratory) was used for the preparation of urease-conjugated antibody by avidin-biotin method as in Example 1.

Figure 13:
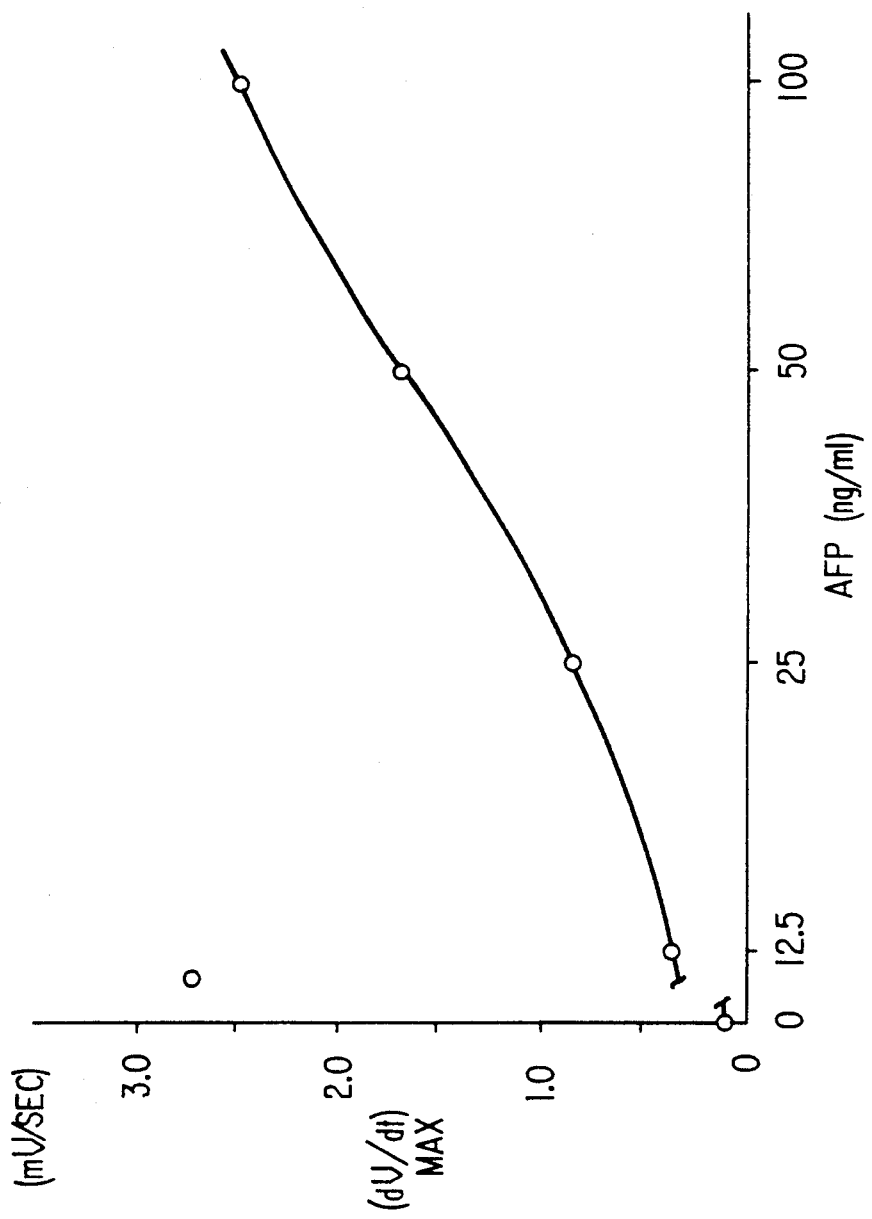

Using these solid phase and conjugated antibody, the calibration curve for AFP was prepared as in Example 1 and the result was shown in FIG. 13. As obvious from FIG. 13, AFP of about 10 ng/ml can easily be measured by the present method.

Obviously, numerous modifications and variations of the present invention are possible in light of the above teachings. It is therefore to be understood that withing the scope of the appended claims, the invention may be practiced otherwise than as specifically described herein.

What is claimed is:

1. A method for measuring the amount of an analyte substance present in a sample, comprising:
   (i) contacting the product of a completed analytereceptor reaction bound to a solid phase with a substrate solution, wherein said substrate is capable of changing the pH of said substrate solution as a function of its reaction with said product, wherein said solid phase is provided in a non-touching spaced relationship with and facing a pH sensitive surface of a pH electrode such that the space between the two is not greater than 1 mm; and
   (ii) monitoring the pH change of said substrate solution enclosed in said space.

2. The method of claim 1, wherein said analyte-receptor reaction is an antigen-antibody reaction.

3. The method of claim 1, wherein said substrate reaction with said product is an enzymatic reaction and wherein said product is labeled with an enzyme.

4. An apparatus for measuring the amount of an analyte substance present in a sample by contacting the product of a completed analyte-receptor reaction bound to a solid phase with a solution containing a substrate capable o changing the pH of said substrate solution upon its reaction with said product, wherein change in the pH of said substrate is used to measure the amount of analyte in the sample, said apparatus comprising:
   a) a cell means having an inlet means and an outlet means for said substrate solution;
   b) a pH electrode having a pH sensitive surface housed in said cell means;
   c) a pump means for supplying said substrate solution into said cell means;
   d) a solid phase in said cell means comprising a small-diameter tube having an inner diameter of not more than 2.0 mm, said small-diameter tube having fixed on its inner wall a first receptor which can specifically bind said analyte; and
   e) a means for positioning said solid phase in a non-touching spaced relationship with the facing the pH sensitive surface of said pH electrode such that the distance between the two is not more than 1 mm.

5. The apparatus of claim 4, wherein said pH electrode is a pH-sensitive field-effect transistor having a mutual conductance of at least 50 μΩ and a pH-sensitivity at 25° C. of 40–60 mV/pH.

6. The apparatus of claim 4, wherein the solid phase comprises an antibody and a labeled second receptor or labeled analyte which is labeled with an enzyme.

* * * * *

UNITED STATES PATENT AND TRADEMARK OFFICE
CERTIFICATE OF CORRECTION

PATENT NO. : 5,066,582

DATED : NOVEMBER 19, 1991

INVENTOR(S) : HITOSHI TSURUTA ET AL

It is certified that error appears in the above-identified patent and that said Letters Patent is hereby corrected as shown below:

Column 6, line 31, delete "$\mu\Omega$, insert --$\mu\mho$--;
        line 32, delete "$\mu\Omega$, insert --$\mu\mho$--;
        line 38, delete "$\mu\Omega$, insert --$\mu\mho$--.

Column 10, line 29, delete "$\mu\Omega$, insert --$\mu\mho$--.

Claim 5, line 3, delete "$\mu\Omega$", insert --$\mu\mho$--.

Signed and Sealed this

Twenty-fourth Day of August, 1993

*Attest:*

BRUCE LEHMAN

*Attesting Officer*     *Commissioner of Patents and Trademarks*